United States Patent
Ling et al.

(10) Patent No.: US 9,173,278 B2
(45) Date of Patent: Oct. 27, 2015

(54) COUNTER WEIGHT MEANS FOR A CROSS ARM OF X-RAY EQUIPMENT AND A CORRESPONDING X-RAY EQUIPMENT

(71) Applicant: GE Medical Systems Global Technology Company LLC, Waukesha, WI (US)

(72) Inventors: Zhenggang Ling, Cheng Du (CN); Yicheng Wang, Beijing (CN); Zhengjun Wang, Chongqing (CN)

(73) Assignee: GE MEDICAL SYSTEMS GLOBAL TECHNOLOGY COMPANY LLC, Waukesha, WI (US)

( * ) Notice: Subject to any disclaimer, the term of this patent is extended or adjusted under 35 U.S.C. 154(b) by 147 days.

(21) Appl. No.: 13/930,469

(22) Filed: Jun. 28, 2013

(65) Prior Publication Data

US 2014/0003585 A1    Jan. 2, 2014

(30) Foreign Application Priority Data

Jun. 29, 2012    (CN) ...................... 2012 2 0310852 U

(51) Int. Cl.
*A61B 6/00* (2006.01)
*H05G 1/02* (2006.01)

(52) U.S. Cl.
CPC ........ *H05G 1/02* (2013.01); *A61B 6/447* (2013.01); *A61B 6/4441* (2013.01)

(58) Field of Classification Search
CPC ...... A61B 6/44; A61B 6/4429; A61B 6/4441; A61B 6/447; A61B 6/4435
See application file for complete search history.

(56) References Cited

U.S. PATENT DOCUMENTS

| | | | | |
|---|---|---|---|---|
| 3,254,223 | A * | 5/1966 | Koerner et al. | 378/181 |
| 4,288,700 | A | 9/1981 | Barrett | |
| 4,339,825 | A | 7/1982 | Barrett | |
| 4,358,856 | A * | 11/1982 | Stivender et al. | 378/167 |
| 4,363,128 | A * | 12/1982 | Grady et al. | 378/181 |
| 4,955,046 | A * | 9/1990 | Siczek et al. | 378/197 |

* cited by examiner

*Primary Examiner* — Thomas R Artman
(74) *Attorney, Agent, or Firm* — GE Global Patent Operation; Marc A. Vivenzio

(57) ABSTRACT

A gravity balance device for a cross arm of X-ray equipment, the gravity balance device is mounted within the cross arm for maintaining gravity balance of the cross arm, the gravity balance device comprises a counter weight module, configured to move along in a direction opposite to a moving direction of a tube of the X-ray equipment.

12 Claims, 2 Drawing Sheets

COUNTER WEIGHT MEANS FOR A CROSS ARM OF X-RAY EQUIPMENT AND A CORRESPONDING X-RAY EQUIPMENT

TECHNICAL FIELD

Embodiments of the present invention relate to the art of medical imaging devices, in particular, the art of X-ray equipment.

BACKGROUND OF THE INVENTION

A cross arm in a medical X-ray equipment mainly performs the function of supporting a tube and a detector; during use, the cross arm needs to be rotated for taking different X-ray films or images. FIG. 1A shows an X-ray equipment 100 when a cross arm 101 of the medical X-ray equipment 100 is in a horizontal position; FIG. 1B shows the X-ray equipment 100 when the cross arm 101 rotates to a vertical position. When the cross arm 101 is rotated, the distance from a tube 103 to a detector 104 (SID) also needs to be adjusted; since the detector 104 is fixed and cannot move along the cross arm, the adjustment of SID can be realized only by moving the tube 103 along a guide 102 on the cross arm 101. When the tube is moving relatively, the gravity balance of the whole cross arm is broken; here an external force is needed to keep balance of the cross arm, so as to avoid the cross arm from rotating, to keep the center of gravity of the cross arm unchanged during the moving of the tube.

In the prior art, a motor is adopted to control rotation of the cross arm. When SID is adjusted, the motor will bear a higher moment caused by gravity imbalance.

However, for that X-ray equipment in which rotation of a cross arm is manually controlled, the prior art gives no corresponding inspiration regarding how to keep the cross arm balanced when SID is adjusted.

SUMMARY OF THE INVENTION

According to an embodiment of the present invention, there is provided a gravity balance for a cross arm of X-ray equipment. The gravity balance is mounted within the cross arm for maintaining gravity balance of the cross arm, and a counter weight module, configured to move along in a direction opposite to the direction in which a tube of X-ray equipment moves.

DETAILED DESCRIPTION OF THE INVENTION

Figure 1A:
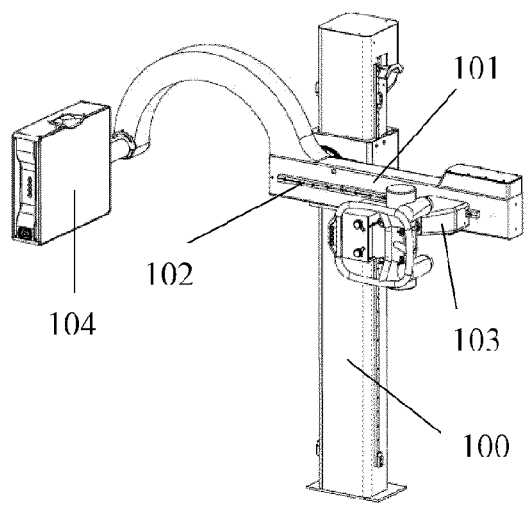
FIG. 1A is a schematic diagram of positions of a cross arm and a tube when a chest position is taken by a medical X-ray equipment.
Figure 1B:
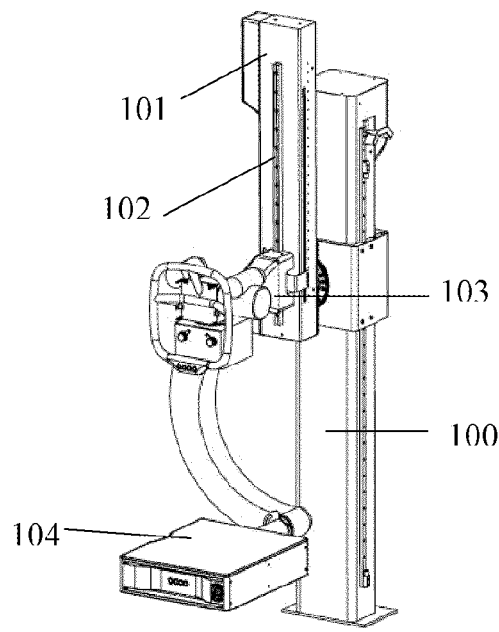
FIG. 1B is a schematic diagram of positions of a cross arm and a tube when a decubitus position is taken by a medical X-ray equipment.

The present invention is further described below in reference to the drawings and the embodiments.

An embodiment of the present invention provides a novel gravity balance device for a cross arm of X-ray equipment, so as to solve the problem of gravity balance of a cross arm for an X-ray equipment whose rotation is manually controlled, which problem cannot be solved by the prior art, and the problem that a motor for electrically controlling rotation of a cross arm of an X-ray equipment needs to bear a higher moment.

An embodiment of the present invention is designed to provide a gravity balance device for a cross arm of X-ray equipment, the device is mounted within the cross arm for maintaining gravity balance of the cross arm, wherein the gravity balance device comprises a counter weight module, capable of moving along in a direction opposite to the direction in which a tube of X-ray equipment moves.

In an embodiment, the gravity balance device for a cross arm of X-ray equipment, further comprises a chain for impelling the tube and the counter weight module to move, a first sprocket, engaged with the chain so as to impel the chain to move, a guide of the counter weight module, for enabling the counter weight module to move along it, and a braking shaft mounted on the cross arm; a second sprocket, engaged with the chain and capable of rotating about the braking shaft.

In an embodiment, the cross arm of the X-ray equipment is configured to serve as a gravity balance-, wherein a part of the chain which is located at one side of the first and second sprockets is used to impel the counter weight module to move, and another part of the chain which is located at another side of the first and second sprockets is used to impel the tube to move.

In an embodiment, a gravity balance device for a cross arm of X-ray equipment, further comprising a brake, which brake is fixedly mounted on the cross arm and is used to apply a braking to the braking shaft when the tube needs to stop moving.

In an embodiment, the present invention is designed to provide a gravity balance device for a cross arm of X-ray equipment, wherein the counter weight module has a same weight with the tube.

In an embodiment, the present invention is designed to provide a gravity balance device for a cross arm of X-ray equipment, wherein the cross arm is a U-arm.

An embodiment of the present invention further provides an X-ray equipment, comprising the gravity balance device for the cross arm of X-ray equipment according to the present invention.

Compared with the prior art, the gravity balance device for the cross arm of X-ray equipment and the corresponding X-ray equipment, as provided by embodiments of the present invention, can solve the problem of how to realize gravity balance for the cross arm of the X-ray equipment whose rotation is manually controlled, greatly reduce production cost of the cross arm for the reason that the balance device does not use electrical elements, improve the cross arm for the reason that the gravity balance device can also be used in a cross arm of X-ray equipment whose rotation is electrically controlled; eliminating risks of exceptional inclination and rotation in an imbalance state of the cross arm; and improving the security of equipment.

Figure 2:
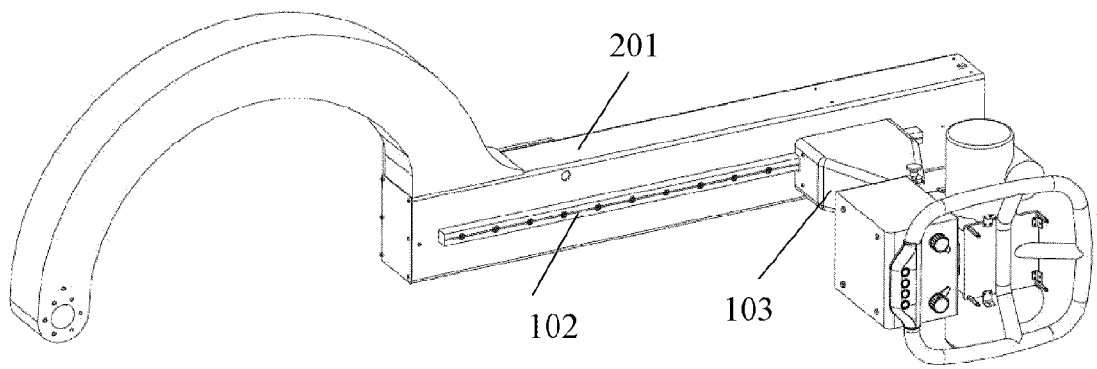
FIG. 2 is a schematic diagram of the cross arm of the medical X-ray equipment according to an embodiment of the present invention.

FIG. 2 shows an overall structure of the cross arm of the medical X-ray equipment in an embodiment the present invention, comprising a housing 201 of the cross arm, a linear guide 102 fixedly mounted on the housing 201, and a tube 103 capable of moving along the linear guide 102. The gravity balance device for the cross arm as proposed by an embodiment the present invention is installed within the housing 201 of the cross arm.

The gravity balance device for the cross arm of X-ray equipment as provided by embodiments of the present invention and corresponding X-ray equipment, solve the problem of self-balancing the cross arm of X-ray equipment, thus improving the security of equipment, reducing production cost of the cross arm, expanding application scope of the cross arm, and eliminating risk of accidents due to exceptional inclination and rotation in an imbalance state of the cross arm.

Figure 3:
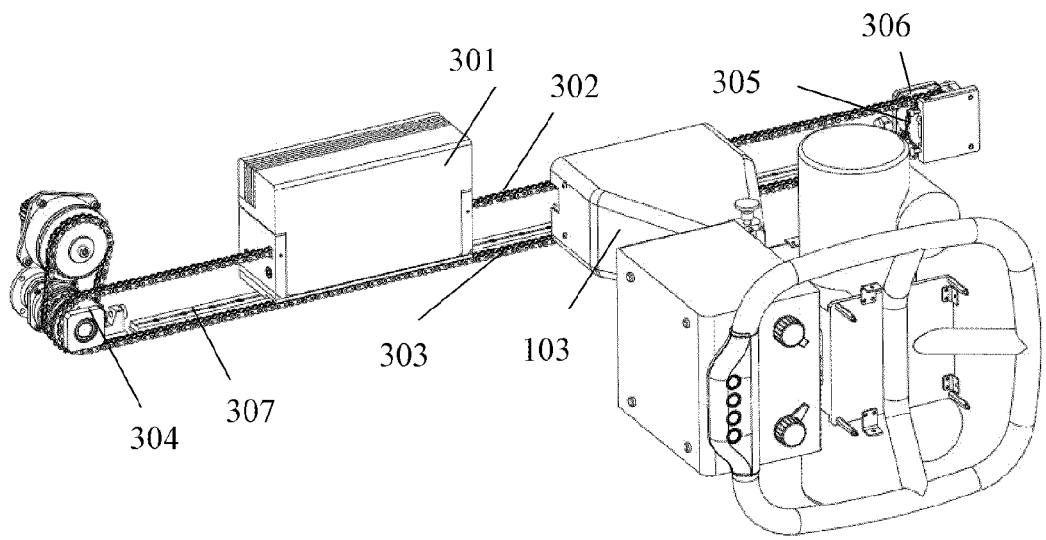
FIG. 3 is a front view of the gravity balance device for the cross arm of X-ray equipment according to an embodiment of the present invention.
Figure 4:
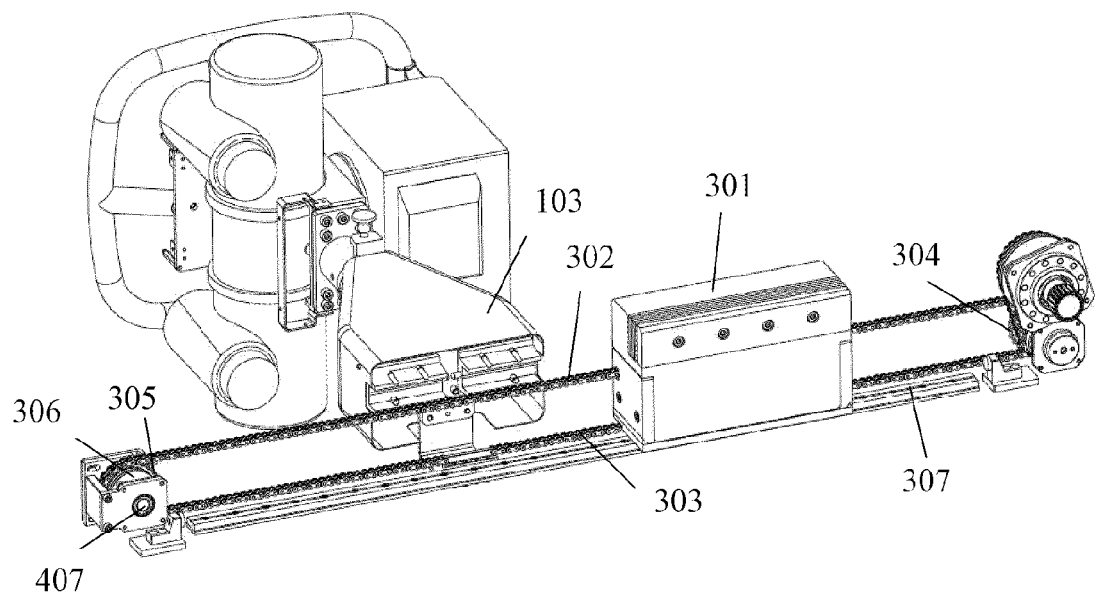
FIG. 4 is a rear view of the gravity balance device for the cross arm of X-ray equipment according to an embodiment of the present invention.

FIG. 3 shows a front view of the gravity balance device for the cross arm of X-ray equipment as proposed by an embodiment of the present invention, including the angle of watching when an operator of X-ray equipment is operating the equipment. FIG. 4 shows a rear view of the gravity balance device for the cross arm of X-ray equipment according to an embodiment of the present invention; this view depicts the visual angle opposite to the angle of watching when an operator of the X-ray equipment is operating the equipment. In order to clearly show the specific structure of the gravity balance device, FIGS. 3 and 4 omit the housing of the cross arm.

As seen from FIGS. 3 and 4, the gravity balance device comprises a counter weight module 301; when the tube 103 is moving, the counter weight module 301 can move along in a direction opposite to the direction in which the tube 103 moves.

In an embodiment, the movement is realized in a manner of a sprocket plus a chain. A first sprocket 304 can provide power for moving the tube 103 and the counter weight module 301, and a second sprocket 305 can rotate about a shaft 407 mounted on the cross arm The first sprocket 304 and the second sprocket 305 are both engaged with a chain. After the chain is engaged with the first sprocket 304 and the second sprocket 305, the chain divides into two segments, segment 302 and segment 303, wherein the segment 302 is used to impel the counter weight module 301 to move, and the segment 303 is used to impel the tube 103 to move. Since the first sprocket 304 impels the segment 302 and the segment 303 of the chain to move in opposite directions when rotating, it can be realized that, when the tube 103 is moving, the counter weight module 301 moves on a guide 307 of the counter weight module in a direction opposite to the direction in which the tube 103 moves.

In order to keep the center of gravity of the cross arm unchanged during the moving of the tube 103, it is only needed to design the counter weight module 301 to have a same weight with the tube 103.

In addition, when the tube needs to stop at an appropriate position at which the tube has arrived, a brake 306, which is provided on the top of the shaft 407 where the second sprocket 305 is located, will apply a braking force to the shaft 407, then the second sprocket 305 cannot rotate, and the tube 103 and the counter weight module 301 will stop moving at the same time.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A gravity balance device for a cross arm of X-ray equipment, the gravity balance device is mounted within the cross arm for maintaining gravity balance of the cross arm, the gravity balance device comprising:
   a counter weight module configured to move along in a direction opposite, with respect to a center of rotation of the cross arm, to a moving direction of a tube of the X-ray equipment;
   a chain configured to impel the tube and the counter weight module to move;
   a first sprocket engaged with the chain; and
   a second sprocket engaged with the chain,
   wherein a part of the chain which is located at a side of the first sprocket and at a side of the second sprocket is configured to impel the counter weight module to move, and another part of the chain which is located at another side of the first sprocket and at another side of the second sprocket is configured to impel the tube to move.

2. The gravity balance device according to claim 1, further comprising:
   a guide for the counter weight module, wherein the counter weight module moves along the guide; and
   a braking shaft mounted on the cross arm,
   wherein the first sprocket is configured to impel the chain to move, and the second sprocket is configured to rotate about the braking shaft.

3. The gravity balance device according to claim 2, further comprising:
   a brake fixedly mounted on the cross arm and configured to apply a braking to the braking shaft when the tube needs to stop moving.

4. The gravity balance device according to claim 1, wherein the counter weight module has a same weight as the tube.

5. The gravity balance device according to claim 1, wherein the cross arm is a U-arm.

6. The gravity balance device according to claim 1, wherein the counter weight module is further configured to move between the center of rotation and an end of the cross arm.

7. An X-ray equipment, comprising:
   a cross arm;
   a tube;
   a gravity balance device mounted within the cross and configured to maintain a gravity balance of the cross arm;
   a counter weight module configured to move along in a direction opposite, with respect to a center of rotation of the cross arm, to a moving direction of the tube;
   a chain configured to impel the tube and the counter weight module to move;
   a first sprocket engaged with the chain; and
   a second sprocket engaged with the chain,
   wherein a part of the chain which is located at one side of the first sprocket and one side of the second sprocket is configured to impel the counter weight module to move, and another part of the chain which is located at another side of the first sprocket and at another the side of the second sprocket is configured to impel the tube to move.

8. The X-ray equipment according to claim 7, further comprising:
   a guide for the counter weight module, wherein the counter weight module moves along the guide; and
   a braking shaft mounted on the cross arm,
   wherein the first sprocket is configured to impel the chain to move, and the second sprocket is configured to rotate about the braking shaft.

9. The X-ray equipment of claim according to claim 8, further comprising:
    a brake fixedly mounted on the cross arm and configured to apply a braking to the braking shaft when the tube needs to stop moving.

10. The X-ray equipment according to claim 8, wherein the cross arm is a U-arm.

11. The X-ray equipment according to claim 7, wherein the counter weight module has a same weight as the tube.

12. The X-ray equipment according to claim 7, wherein the counter weight module is further configured to move between the center of rotation and an end of the cross arm.

\* \* \* \* \*

UNITED STATES PATENT AND TRADEMARK OFFICE
CERTIFICATE OF CORRECTION

PATENT NO.      : 9,173,278 B2
APPLICATION NO. : 13/930469
DATED           : October 27, 2015
INVENTOR(S)     : Ling et al.

It is certified that error appears in the above-identified patent and that said Letters Patent is hereby corrected as shown below:

In the claims

In Column 4, Line 58, in Claim 7, delete "another the" and insert -- another --, therefor.

In Column 5, Line 1, in Claim 9, delete "of claim according" and insert -- according --, therefor.

Signed and Sealed this
Fifth Day of July, 2016

Michelle K. Lee
*Director of the United States Patent and Trademark Office*